United States Patent [19]

Holdom et al.

[11] Patent Number: 4,920,215
[45] Date of Patent: Apr. 24, 1990

[54] ANTIBIOTIC PRODUCED BY FERMENTATION

[75] Inventors: Kelvin S. Holdom, Ramsgate; John C. Ruddock, Canterbury, both of England; Junsuke Tone; Hiroshi Maeda, both of Chita, Japan; Martin R. Jefson, Stonington, Conn.

[73] Assignee: Pfizer Inc., New York, N.Y.

[21] Appl. No.: 133,752

[22] Filed: Dec. 16, 1987

[30] Foreign Application Priority Data

Jan. 9, 1987 [GB] United Kingdom ............... 8700513

[51] Int. Cl.$^5$ .................. C07G 11/00; C07G 3/00; A61K 35/00; C12R 1/365
[52] U.S. Cl. ............................ 536/16.8; 536/18.5; 424/116; 424/122; 424/442; 435/872; 435/886; 514/867
[58] Field of Search ............... 536/16.8, 18.5; 424/116, 122, 442; 435/872, 886

[56] References Cited

U.S. PATENT DOCUMENTS 3,067,099 12/1962 McCormick et al. ............... 435/72
4,495,179 1/1985 Hoehn et al. ........................ 514/9
4,717,714 1/1988 Boeck et al. ..................... 536/16.8

OTHER PUBLICATIONS

Bergey's Manual of Systematic Bacteriology, vol. 2, Williams & Wilkins, 1986, p. 1469.
ATCC—Catalogue of Bacteriophages, 17th Edition, 1989, p. 16.

*Primary Examiner*—Ronald W. Griffin
*Assistant Examiner*—Everett White

*Attorney, Agent, or Firm*—Peter C. Richardson; J. Trevor Lumb; Robert K. Blackwood

[57] ABSTRACT

The antibiotic of the formula:

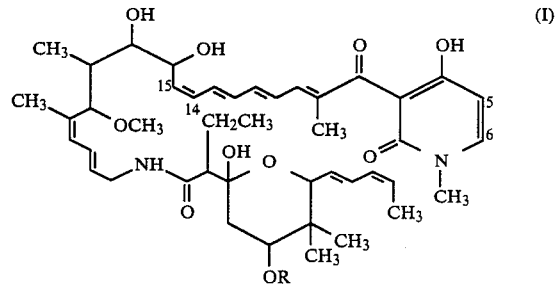

wherein R is

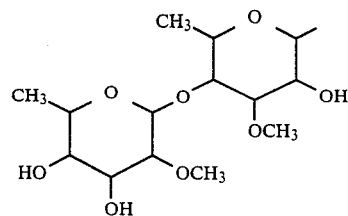

The antibiotic is useful for the treatment of swine dysentery and for promoting growth and/or increasing the efficiency of food utilization in poultry, swine and ruminants.

6 Claims, No Drawings

ANTIBIOTIC PRODUCED BY FERMENTATION

This invention is concerned with a new antibiotic compound of the efrotomycin group, to compositions containing said compound, and to a method of using said compound. More particularly, this invention is concerned with a compound which is closely related to the efrotomycin family of antibiotics which includes such agents as efrotomycin, mocimycin, aurodox, heneicomycin, factumycin, azdimycin and kirrothricin. This subject has been reviewed by Parmeggiani et al, "Properties and Action of Kirromycin (Mocimycin) and Related Antibiotics", Top. Antibiot. Chem., 5, 159–221, 1980.

In the search for new antibiotics, structural modification of known antibiotics is attempted whenever possible. This approach is limited, however, to modifications which retain the desired activity. Many antibiotics, including the efrotomycins, have such complex structures that even small changes can be difficult to make by chemical means. The discovery of new antibiotics produced by fermentation processes continues, therefore, to be of great importance even in cases where the antibiotic, once recognised, is quite similar to a previously known antibiotic.

The known antibiotics listed above are active against a range of Gram-positive and Gram-negative bacteria, and have been employed with varying degrees of success in the treatment of bacterial infections and in promoting growth and/or improving feed efficiency in farm animals.

Among a number of conditions which can be treated with these agents are swine dysentery and enteritis.

Swine dysentery is one of the most common swine diseases diagnosed in the United States. Additionally, the disease is prevalent in many other countries and annually causes considerable losses in stock to swine growers around the world. It has recently been discovered that a large spirochete is the causative organism of the disease. This organism, *Treponema hyodysenteriae*, has now been isolated and shown to be capable of producing the disease [Harris, D. L. et al. "Swine Dysentery-1, Innoculation of Pigs with *Treponema hyodysenteriae* (New Species) and Reproduction of the Disease", *Vet. Med/SAC*, 67, 61–64, 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "over-eating disease" in sheep, is a condition caused by *C. perfringens* infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Micro-organisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. For a more detailed discussion, see Leng in "Physiology of Digestion and Metabolism in the Ruminant", "Phillipson et al., Eds., Oriel Press", Newcastle-upon-Tyne, England, 1970, pp. 408–410.

The relative efficiency of volatile fatty acid utilization is discussed by McCullough in "Feedstuffs", June 19, 1971, page 19; Eskeland et al. in *J. An. Sci.*, 33, 282, 1971; and Church et al. in "Digestive Physiology and Nutrition of Ruminants", Vol. 2, 1971, pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

This invention is concerned with the new acidic antibiotic designated U.K. No. 69,753, produced by the submerged aerobic propagation in aqueous nutrient media of the microorganism *Amycolatopsis orientalis* ATCC 53550 isolated from a soil sample from England. This antibiotic and its cationic salts are active against a variety of Gram-positive and Gram-negative bacteria. They are effective in controlling swine dysentery and enteritis as well as being effective in promoting growth and increasing the efficiency of feed utilisation in poultry, swine, and ruminants.

The microorganism designated herein as *Amycolatopsis orientalis* ATCC 53,550, and being useful for the preparation of the antibiotic U.K. No. 69,753, was isolated from a soil sample collected in Yorkshire, United Kingdom. Biologically pure cultures of this microorganism form a part of this invention, as do mutants and recombinant forms thereof which are capable of producing the antibiotic of the invention.

A culture of ATCC 53550, designated herein as N731-15, was planted from a slant into ATCC no. 172 broth and grown for four days at 28° C. on a shaker. It was then centrifuged for 20 minutes, washed three times with sterile distilled water, and inoculated on media commonly used for identification of members of the Actinomycetales. The culture was incubated at 28° C. and the results were read at varying times but most commonly were taken at fourteen days. The colours were described in common terminology, but exact colours were determined by comparisons with colour chips from the Colour Harmony Manual, fourth edition. The methods of whole-cell amino acid and sugar analyses are those described in Becker, B. et al., Appl. Microbiol., 12, 421–423, 1964, and in Lechevalier, M. P., J. Clin. Med., 71, 934–944, 1968. About 30 grams of autoclaved, wet mycelium were used for mycolate analyses, using the method described by Lechevalier, M. P. et al. in J. Bacteriol., 105, 313–318, 1971. For phospholipid analyses, the method described by Minnikin, D. E. et al. in J. Microbiol. Method, 2, 233–241, 1984, is used.

Identification media used for the characterisation of the culture and references for their composition or supplier are as follows:

1. Yeast Extract-Malt Extract Agar - (ISP medium no. 2, Difco).
2. Oatmeal Agar - (ISP medium no. 3, Difco).

3. Inorganic Salts-Starch Agar - (ISP medium no. 4, Difco).

4. Glycerol-Asparagine Agar - (ISP medium no. 5, Difco).

5. Czapek-Sucrose Agar - S. A. Waksman, The Actinomycetes, Vol. 2, medium no. 1, p. 328, 1961.

6. Glucose-Asparagine Agar - Ibid, medium no. 2, p. 328.

7. Emerson's Agar - Ibid, medium no. 28, p. 331.

8. Nutrient Agar - Ibid, medium no. 14, p. 330.

9. Bennett's Agar - Ibid, medium no. 30, p. 331.

10. Gordon and Smith's Tyrosine Agar - R. E. Gordon and M. M. Smith, *J. Bact.*, 69, 147-150, 1955.

11. Calcium Malate Agar; S. A. Waksman, *Bact. Rev.* 21, 1-29, 1957.

12. Casein Agar - Ibid.

13. Gelatin Agar - R. E. Gordon and J. M. Mihm, *J. Bact.*, 73, 15-27, 1957.

14. Starch Agar - Ibid.

15. Potato Carrot Agar - M. P. Lechevalier, *J. Lab. and Clinical Med.*, 71, 934-944, 1968, but use only 30 g potatoes, 2.5 g carrots and 20 g agar.

16. 2% Tap Water Agar.

The observations of growth and appearance of the organism were as follows:

Yeast Extract-Malt Extract Agar

Growth good, cream to pale yellowish (2ca, 2ea); raised, wrinkled, without aerial mycelium; reverse pale yellowish (2ea, 2ga); soluble pigment yellowish brown (3lc).

Oatmeal Agar

Growth poor to moderate, cream (2ca), thin, smooth, no aerial mycelium; reverse cream (2ca); soluble pigment cream (2ca).

Inorganic Salts - Starch Agar

Growth poor, colourless to cream (2ca), thin, smooth, without aerial mycelium; reverse same as surface; no soluble pigment.

Glycerol-Asparagine Agar

Growth poor to moderate, cream (2ca), slightly raised, smooth to granular, no aerial mycelium; reverse cream to pale yellowish (2ca, 2ea); no soluble pigment.

Czapek-Sucrose Agar

Growth poor to moderate, cream (2ca), thin, smooth, no aerial mycelium; reverse colourless to cream (2ca); no soluble pigment.

Glucose-Asparagine Agar

Growth moderate, cream (2ca), slightly to moderately raised, smooth to granular, no aerial mycelium; reverse cream to pale yellowish (2ca, 2ea); no soluble pigment.

Emerson's Agar

Growth good to excellent; cream, pale yellowish to yellowish (2ca, 2ea, 2ga); raised, wrinkled, no aerial mycelium; reverse dark yellowish (2ic, 2nc); soluble pigment yellowish brown (3lc).

Nutrient Agar

Growth moderate, pale yellowish (2ea), slightly raised, smooth, no aerial mycelium; reverse yellowish (2ia, 2la); no soluble pigment.

Bennett's Agar

Growth good, cream (2ca), raised, smooth to wrinkled, no aerial mycelium; reverse yellowish (2ga, 2ia); soluble pigment pale yellowish (2ea).

Gordon and Smith's Tyrosine Agar

Growth moderate, dark yellowish to brown (2le, 4ng), slightly to moderately raised, smooth but wrinkled toward end of streak, no aerial mycelium; reverse brown (3ne); soluble pigment dark brown (4pl).

Calcium Malate Agar

Growth moderate, cream (2ca), thin to moderately raised, smooth to granular, no aerial mycelium; reverse pale yellowish (2ea): no soluble pigment.

Casein Agar

Growth good, pale yellowish to brown (2ea, 4lg), moderately raised, wrinkled, no aerial mycelium; reverse brown (3le); soluble pigment dark brown (4ni).

Gelatin Agar

Growth good, yellowish (2ga), moderately raised, smooth but wrinkled toward edge, no aerial mycelium; reverse yellowish (2ga); no soluble pigment.

Starch Agar

Growth good, yellowish (2ga), moderately raised, smooth but wrinkled toward end of streak, no aerial mycelium; reverse yellowish (2ec, 2ic); no soluble pigment.

Potato Carrot Agar

Growth poor to moderate, cream (2ca); thin smooth, no aerial mycelium; reverse cream (2ca); no soluble pigment.

Tap Water Agar

Growth poor, colourless to cream (1½ca), thin, smooth, no aerial mycelium; reverse same as surface; no soluble pigment.

Morphological Properties

Culture N731-15 failed to produce an aerial mycelium or spores on any of the media used, even upon an incubation of up to four weeks. On inorganic salts-starch agar it produced short chains of spore-like structures along some segments of the substrate hyphae, but they might represent condensation of the cytoplasm. On tap water agar, it developed terminal swellings at the tips of the substrate hyphae, which resembled spores. The vegetative hyphae on oatmeal agar were narrow, branched, and measured 0.4 to 0.9 μm in diameter.

Biochemical Properties

The results of biochemical properties and acid production from carbohydrates are shown in Table 1 and Table 2.

TABLE 1

| Biochemical properties of culture N731-15 | | | |
|---|---|---|---|
| Decomposition of: | | Growth in: | |
| Adenine | + | Lysozyme broth | − |
| Calcium malate | + | 5% NaCl | + |
| Casein | + | Clearing and coagulation of: | |
| Cellulose | − | Skim milk | + |
| Hypoxanthine | + | Utilization of: | |
| Tyrosine | + | Acetate | + |
| Xanthine | + | Benzoate | − |
| Hydrolysis of: | | Citrate | + |
| Esculin | − | Dextrin | − |
| Hippurate | − | Lactate | + |
| Starch | + | Malate | + |
| Production of: | | Mucate | − |
| Hydrogen sulfide | + | Oxalate | − |
| Melanin | − | Phenol | − |
| Production of: | | Propionate | + |
| Gelatinase | + | Pyruvate | + |
| Nitrate reductase | + | Succinate | + |
| Phosphatase | + | | |
| Urease | + | | |

TABLE 2

Acid Production from (and Utilization of) Carbohydrates of Culture N731-15[a]

| | | | |
|---|---|---|---|
| Glucose | +(+) | Glycerol | +(+) |
| Arabinose | +(+) | Lactose | −(−) |
| Fructose | +(+) | Maltose | −(+) |
| Inositol | −(−) | Mannose | +(+) |
| Mannitol | +(+) | Melezitose | −(−) |
| Raffinose | +(+)[b] | Melibiose | −(−) |
| Rhamnose | +(+) | α-Methyl-D-glucoside | −(−) |
| Sucrose | −(+) | Ribose | +(+) |
| Xylose | +(+) | Salicin | −(+) |
| Adonitol | +(+) | Sorbitol | +(+) |
| Cellobiose | +(+) | Sorbose | −(−) |
| Dulcitol | −(+) | Starch | +(+) |
| Erythritol | +(+) | Trehalose | +(+) |
| Galactose | +(+) | | |

[a]Gordon, R. E. et al., Int. J. Syst. Bacteriol., 24, 54–63, 1974.
[b]The culture did not utilize raffinose when the method of Shirling and Gottlieb (Int. J. Syst. Bacteriol., 16, 313–340, 1966) was used.

Temperature Relationships

The culture showed no growth at 10°, 37° or 45° C., good growth at 20° C., and good to excellent growth at 28° C.

Cell Wall Analyses

The whole-cell hydrolysates contained meso-diaminopimelic acid, galactose and arabinose.

Mycolate Analysis

The cell wall contained no mycolates.

Phospholipid Analysis

The extracts of the cell membrane contained phosphatidylethanolamine, phosphatidylglycerol and diphosphatidylglycerol.

In summary, culture N731-15 is characterised by the cream to pale yellowish substrate mycelium, the lack of aerial mycelium, and the lack of spores. The following biochemical tests were positive: decomposition of adenine, calcium malate, casein, hypoxanthine, tyrosine, and xanthine; hydrolysis of starch; production of hydrogen sulfide; production of gelatinase, nitrate reductase, phosphatase, and urease; growth in 5% NaCl; clearing and coagulation of milk; utilization of acetate, citrate, lactate, malate, propionate, pyruvate, and succinate. Negative characteristics were: decomposition of cellulose; hydrolysis of esculin and hippurate; production of melanin; growth in lysozyme broth; utilization of benzoate, dextrin, mucate, oxalate and phenol. Acid was produced from glucose; arabinose, fructose, mannitol, raffinose, rhamnose, xylose, adonitol, cellobiose, erythritol, galactose, glycerol, mannose, ribose, sorbitol, starch and trehalose; but not from inositol, sucrose, dulcitol, lactose, maltose, melezitose, melibiose, α-methyl-D-glucoside, salicin and sorbose. The cell wall, which contained meso-diaminopimelic acid, galactose and arabinose, is of the type IV, as defined by Lechevalier and Lechevalier. The culture contained no mycolates but contained phosphatidylethanolamine in addition to phosphatidylglycerol and diphosphatidylglycerol - a type PII phospholipid pattern. These characteristics fit into the description of the genus Amycolatopsis recently proposed by Lechevalier et al. in Int. J. Syst. Bacteriol., 36, 29–37, 1986.

Among the species described therein, *A. orientalis* closely resembles culture N731-15 in most of the biochemical tests. Several differences were noted. Culture N731-15 differs from *A. orientalis* in decomposition of adenine, lack of esculinase, lack of acid production from inositol, lactose and α-methyl-D-glucoside. On the basis of the data mentioned above, culture N731-15 is considered as a new strain of *Amycolatopsis orientalis* (Pittenger & Brigham) Lechevalier, Prauser, Labeda & Ruan. It has been deposited at the American Type Culture Collection 12301 Parklawn Drive, Rockville, Maryland 20852, U.S.A. under the provisions of the Budapest Treaty on 9th October, 1986 under the accession number ATCC 53550.

Cultivation of *Amycolatopsis orientalis* ATCC 53550 and isolation of the Antibiotic U.K. No. 69,753 may be conducted under conditions similar to those generally employed to produce antibiotics by fermentation. Cultivation preferably takes place in aqueous nutrient media under submerged aerobic conditions with agitation at a temperature of 24° to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles, fishmeal, cotton seed meal, and yeast extract as well as mineral salts such as sodium chloride and calcium carbonate and trace elements such as iron, magnesium, copper, zinc, cobalt and manganese may also be utilized with advantageous results. If excessive foaming is encountered during fermentation, antifoam agents such as polypropylene glycols or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 200 cycles per minute whereas a fermentor is usually run at 100 to 1700 revolutions per minute. Aseptic conditions must, of course, be maintained through the transfer of the organism and throughout its growth.

Inoculum for the preparation of the antibiotic according to this invention may be obtained by employing growth from a slant of the culture or Roux bottles inoculated with the culture. A solid medium suitable for initial growth of the organism on slants and in Roux bottles is ATCC medium no. 172. The growth may be used to inoculate either shake flasks or inoculum tanks or the inoculum tanks may be seeded from the shake flasks. Growth in shaken flasks will generally have reached its maximum in 4 to 5 days whereas inoculum in submerged inoculum tanks will usually be in the most favourable period in 3 to 6 days. Thin-layer chromatography employing silica gel is a useful tool for detecting the antibiotic produced in fermentation media and analyzing the composition of crude and purified materials extracted from the fermentation broths. The chromatograms are developed with chloroform:methyl alcohol 90:10 and the antibiotic compound is visualized by U.V. light at 254 nm.

The antibiotic U.K. No. 69,753 produced by fermentation of *Amycolatopsis orientalis*, ATCC 53550 may be recovered by extracting the whole, unfiltered fermentation broth with an organic solvent such as chloroform, ethyl acetate, methylisobutyl ketone or butanol at the naturally prevailing pH. Alternatively the mycelium can be separated after growth has been completed and the filtrate extracted with an organic solvent. The solvent extract can then be concentrated to a thin syrup and the pure antibiotics obtained by chromatography, or, alternatively, a solvent such as hexane can be added to the solvent extract to precipitate a solid enriched with the antibiotic. This solid can then be processed by chromatography and/or countercurrent distribution to isolate the pure antibiotic.

The preferred method of separation and recovery of the antibiotic compound of the invention is as follows:

The filtrate from a fermentation of *Amycolatopsis orientalis* ATCC 53550 is extracted with ethyl acetate. The solvent extract yields a dark syrup on solvent evaporation under vacuum. Addition of hexane precipitates a dark solid which contains the antibiotic as shown by thin-layer chromatography. Further enrichment of the antibiotic is effected by countercurrent distribution and/or column chromatography. The product may be further purified (and separated from each other) by column chromatography or high performance liquid chromatography, if desired.

The antibiotic compound of the invention is acidic, and will form cationic salts by reaction with basic agents. All such salts, especially those which are non-toxic to mammals, are within the scope of the invention. These salts may be prepared by conventional methods for antibiotics of this class.

In one method, a solution of the antibiotic in a volatile, water immiscible, organic solvent is washed with an aqueous solution containing at least a stoichiometric equivalent, and preferably a large excess, of an appropriate basic agent. After drying the organic solvent solution it is evaporated in vacuo to give the desired cationic salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

Analytical and spectral data for U.K. No. 69,753 indicates that the compound has the following structure:

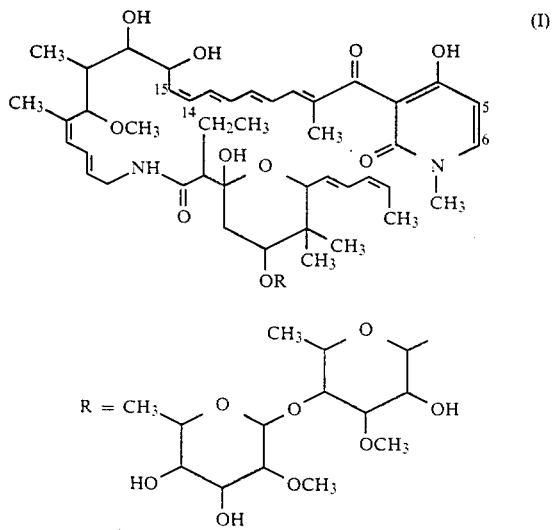

Antibiotic U.K. No. 69,753 exhibits inhibitory action against the growth of a number of microorganisms. In Table 3 below, the results of in vitro tests are summarized. For this test each organism is inoculated in a series of test tubes containing nutrient medium and varying concentrations of Antibiotic U.K. No. 69,753 to determine the minimal concentration of the compound in mcg./ml. which inhibits the growth of the organism over a period of 24 hours (MIC).

TABLE 3

ANTIBACTERIAL ACTIVITY

| Organism | Strain No. | MIC, mcg./ml. Antibiotic UK-69,753 |
|---|---|---|
| *Staphylococcus aureus* | 01A106 | >100 |
|  | 01A539 | >100 |
|  | 01A540 | >100 |
| *Actinomyces pyogenes* | 14D011 | 6.25 |
| *Pasteurella multocida* | 59A006 | 6.25 |
| *Clostridium perfringens* | 10A009 | <0.2 |
| *Bacteroides fragilis* | 78C024 | >100 |
| *Fusobacterium necrophorum* | 84C004 | 12.5 |
| *Treponema hyodysenteriae* | 94A007 | <0.2 |
| *Moraxella bovis* | 93A001 | 6.25 |

Against the gram-negative bacteria such as *Escherischia coli*, MIC values were >50.

From the in vitro data above, it will be seen that U.K. No. 69,753 should be especially useful in the control of T. hydodysenteriae infections in swine.

For the purposes of controlling swine dysentery, the antibiotic U.K. No. 69,753 can be administered to swine alone, or, preferably, in a pharmaceutical composition in which the antibiotic is mixed with a pharmaceutically acceptable carrier or diluent.

Said pharmaceutical composition is prepared according to standard procedures for a veterinary antibiotic. The compound of formula (I) can for example be administered orally in the form of elixers, syrups, solutions and suspensions, e.g. at a level of 1 to 50 mg per kg. of the animal's body weight per day. Solutions and suspensions can be aqueous, non-aqueous or partially aqueous. For parenteral administration, sterile, aqueous solutions are preferred. Parenteral administration includes intramuscular, intraperitoneal, subcutaneous and intravenous use. For intravenous use, the total concentration of solutes should be controlled to render the preparation isotonic.

The proportional ratio of the antibiotic to the pharmaceutically acceptable carrier will depend on the dosage contemplated and the route of administration; however, said proportional ratio will normally be in the range from 1:10 to 2:1, especially 1:5 to 1:1.

Also, when using the antibiotic of the invention to control swine dysentery, it is most convenient to administer the compound by mixing it into the animal's feed. In this case, the antibiotic will be added to the animal's feed at a level which will provide the appropriate daily dosage of the antibiotic, e.g. at a level of 1-100 ppm.

The prescribing veterinarian will ultimately decide the dosage of the antibiotic which will be administered to combat swine dysentery, and this dosage will vary according to the route of administration and the severity of the animal's symptoms.

The value of animal feeds has generally been determined directly by feeding the animal. British patent specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch+17% cellulose+15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml. of the sample is mixed with 1 ml. of 25% metaphosphoric acid. After 10 minutes 0.25 ml. of formic acid is added and the mixture centrifuged at 1500 rpm for 10 minutes. Samples are then analyzed by gas-liquid chromatography by the method of D. W. Kellog, *J. Dairy Science*, 52, 1690, 1969. Peak heights for acetic, propionic and butyric acids are determined for samples from untreated and treated incubation flasks.

When tested by this in vitro procedure, Antibiotic U.K. No. 69,753 at the level of 1.3 micrograms per milliliter gave rise to an increase of about 33% in the production of propionic acid over that produced in the control solution without added Antibiotic U.K. No. 69,753. By comparison, the commercially available compound salinomycin (a polyether antibiotic) at 10 mcg/ml. produced about a 61% increase of propionic acid over the control.

This data shows that the Antibiotic U.K. No. 69,753 will improve feed utilization by ruminants such as cattle and sheep. The compound will also have a similar effect in monogastric animals such as pigs and rabbits. Antibiotic U.K. No. 69,753 may be incorporated in feed compositions as the free acid, sodium salt, potassium salt or mixtures thereof. Crude forms of Antibiotic U.K. No. 69,753 or dried fermentation broth containing the antibiotic may also be incorporated in feed compositions at the desired potency concentrations.

The following Examples illustrate the invention:

EXAMPLE 1

1. Preparation of Inoculum

A sterile aqueous medium having the following composition was prepared.

| Ingredient | Grams/liter |
| --- | --- |
| Glucose | 1 |
| Starch | 24 |
| "Oxoid" (Trade Mark) peptone | 5 |
| "Oxoid" (Trade Mark) yeast | 5 |
| "Lab Lemco" (Trade Mark) meat extract | 3 |
| Calcium Carbonate | 4 (added after adjustment of medium to pH 7) |

Water

Fifty ml of the medium is distributed into 300 ml shake flasks and sterilized at 120° C. and 15 p.s.i. for 30 minutes. After cooling, the medium is inoculated with a vegetative cell suspension from a slant culture of *Amycolatopsis orientalis* ATCC 53550.

The flasks are shaken at 28° C. on a rotary shaker having a displacement of 1½ to 2½ inches and 150 to 200 cycles per minute for two days.

2. Preparation of second stage inoculum

A shake flask containing the grown culture was used to inoculate a 2.8 liter fermentation flask (a "Fernbach") containing one liter of sterile medium of the composition as described above.

The "Fernbach" is shaken at 28° C. on a rotary shaker having a displacement of 1½ to 2½ inches and 150–200 cycles per minute for two days.

3. Production of U.K. No. 69,753

Two "Fernbachs" containing the grown culture were used to inoculate a 130 liter fermentation vessel containing 70 liters of sterile aqueous medium of the following composition:

| Ingredient | Grams/liter |
| --- | --- |
| "Cerelose" (Trade Mark) glucose monhydrate | 10 |
| Corn starch | 10 |
| "Trusoy" (Trade Mark) soya bean flour | 10 |
| Distillers solubles | 5 |
| Sodium chloride | 5 |
| Calcium carbonate | 1 |
| Cobalt chloride | 0.002 |
| Water | |
| pH 7.2 | |

Fermentation was carried out at 28° C. with stirring at 450 revolutions per minute and aeration at one volume of air per volume of broth per minute until substantial activity was observed (based on h.p.l.c. assay), usually after 4–9 days. The antibiotic was detected by using h.p.l.c. conditions as follows:

| Column | Waters $C_{18}$ μ "Bondapak" (Trade Mark) 15 cm × 4.0 mm |
| --- | --- |
| Eluent | 0.1M $KH_2PO_4$ (pH 3.5): acetonitrile, 65:35 |
| Flow | 1.5 ml/min |
| U.V. | 350 nm |
| Temperature | 40° C. |

The retention time of U.K. No. 69,753 under these conditions is typically 11 minutes.

The antibiotic component in the broth and recovery streams may also be detected using silica gel plates developed with chloroform:methanol (90:10) and visualised by U.V. light at 254 nm.

At the end of this time the whole broth was extracted with ethyl acetate, and the solvent was separated and concentrated to yield an oily residue. Addition of hexane (500 ml) precipitated a solid which was separated by filtration (100 mg). High performance liquid chromatography using a Waters "Prep 500" (Trade Mark) system with a $C_{18}$ reversed phase "Prep-Pak" and a mobile phase of 0.1M potassium dihydrogen phosphate:acetonitrile (65:35) gave fractions rich in U.K. No. 69,753. The organic solvent was removed by evaporation under vacuum and the antibiotic extracted into ethyl acetate. Separation of the organic layer and evaporation of the solvent gave U.K. No. 69,753 as a yellow solid (5 mg).

EXAMPLE 2

A 2000 liter fermentor containing 1200 liters of sterile medium of the following composition was inoculated with 70 liters of an inoculum of *Amycolatopsis orientalis*, ATCC 53550, prepared as described in Example 1.

| Ingredient | Grams/liter |
|---|---|
| "Cerelose" (Trade Mark) glucose monohydrate | 10 |
| Corn starch | 10 |
| "Trusoy" (Trade Mark) soya bean flour | 10 |
| Distillers solubles | 5 |
| Sodium chloride | 5 |
| Calcium carbonate | 1 |
| Cobalt chloride | 0.002 |
| Water | |
| pH 7.2 | |

The fermentor was maintained at 28° C. with aeration and stirring at 180 revolutions per minute. After 168 hours the whole broth was filtered and the filtrate extracted with 850 liters of ethyl acetate. The solvate extracts were separated and concentrated under vacuum to 1 liter of an oily residue estimated to contain about 20 g of U.K. No. 69,753 by the h.p.l.c. method described above. On the addition of 4 liters of hexane a solid was precipitated and collected by filtration (128 g).

Fifty-six grams of the said 128 g solid was subjected to a six tube countercurrent distribution using 3:1 ethanol/water (2 liters total volume) as the lower layers and toluene (2 liters) as the upper layers. The antibiotic concentrated in the first three lower layers. These were combined and the ethanol was removed under reduced pressure. The remaining aqueous phase was extracted three times with 1.5 liters methylene chloride. These extracts were combined, dried over sodium sulphate and evaporated to give 12.2 g of a semi-solid. This material was taken up in 300 ml of ethyl acetate and poured slowly into 700 ml of rapidly stirred hexane. After 30 minutes of stirring the resulting precipitate was filtered and vacuum dried to give 9.05 g of a yellow-tan solid. 2.0 g of this solid was subjected to silica gel chromatography eluting with 12:1 chloroform:methanol. After fraction analysis by t.l.c., the pure fractions were combined to yield 0.8 g of U.K. No. 69,753 as an amorphous yellow solid.

When the entire 128 g of crude solid was processed in this fashion, the total yield was 3.9 g of U.K. No. 69,753, m.p. 153°–155° C.

Analysis %:

| Found: | C, 62.88; H, 8.19; N, 2.26; |
|---|---|
| $C_{58}H_{86}N_2O_{18}$ requires: | C, 63.39; H, 7.83; N, 2.55. |

In methanol solution U.K. No. 69,753 has prominent U.V. absorption maxima at 233 and 253 nm. Addition of a few drops of 0.1N sodium hydroxide solution shifts these maxima to 226 and 348 nm and the addition of a few drops of 0.1N HCl gives rise to absorption maxima at 212, 233 and 361 nm. Infra-red spectrum (KBr) $cm^{-1}$: 3416, 2967, 2926, 1648, 1585, 1453, 1414, 1380, 1259, 1083, 1025.

We claim:

1. The antibiotic compound of the formula:

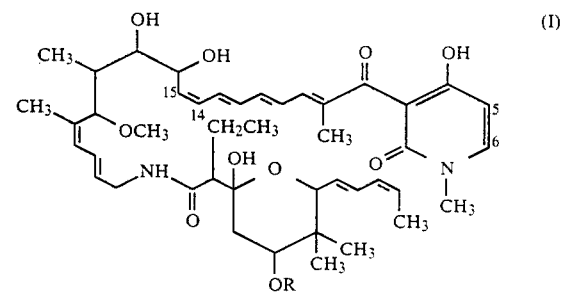

wherein R is

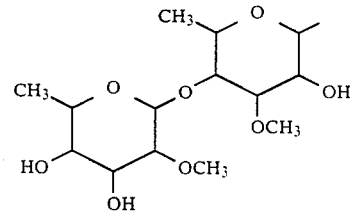

or a salt thereof.

2. A process for preparing the antibiotic compound of claim 1 which comprises cultivating *Amycolatopsis orientalis* having the identifying characteristics of ATCC 53,550 in an aqueous culture media containing an assimilable source of carbon, nitrogen and inorganic salts under submerged aerobic fermentation conditions until a recoverable amount of said antibiotic is obtained.

3. A swine, ruminant or poultry feed composition which comprises the antibiotic compound of claim 1, or a non-toxic salt thereof, and a nutritionally balanced swine, ruminant or poultry feed composition.

4. A method for promoting growth and/or increasing the efficiency of food utilization in poultry, swine or ruminants, comprising administering to said poultry, swine or ruminants an effective amount of the antibiotic compound of claim 1, or a non-toxic salt thereof.

5. A biologically pure culture of the microorganism *Amycolatopsis orientalis* ATCC 53,550.

6. A veterinary composition comprising the antibiotic compound of claim 1, or a non-toxic salt thereof, and a non-toxic diluent or carrier.

* * * * *